(12) United States Patent
Abbott et al.

(10) Patent No.: US 7,345,698 B2
(45) Date of Patent: Mar. 18, 2008

(54) OPTICAL SYSTEM FOR IMAGING DISTORTIONS IN MOVING REFLECTIVE SHEETS

(75) Inventors: Mark M. Abbott, Dundas, MN (US); Eric Hegstrom, Tucson, AZ (US)

(73) Assignee: Litesentry Corporation, Dundas, MN (US)

(*) Notice: Subject to any disclaimer, the term of this patent is extended or adjusted under 35 U.S.C. 154(b) by 764 days.

(21) Appl. No.: 10/377,089

(22) Filed: Feb. 28, 2003

(65) Prior Publication Data

US 2004/0057046 A1 Mar. 25, 2004

Related U.S. Application Data

(63) Continuation-in-part of application No. PCT/US01/27280, filed on Aug. 30, 2001.

(60) Provisional application No. 60/230,281, filed on Sep. 1, 2000.

(51) Int. Cl.
*H04N 7/18* (2006.01)
(52) U.S. Cl. ...................................................... 348/86
(58) Field of Classification Search ................ 348/86, 348/87, 88, 128; 382/149; 356/37.1, 37.2, 356/613, 445
See application file for complete search history.

(56) References Cited

U.S. PATENT DOCUMENTS

| | | | |
|---|---|---|---|
| 4,139,306 A | 2/1979 | Norton | 358/106 |
| 4,223,346 A | 9/1980 | Neiheisel et al. | 358/106 |
| 4,585,343 A * | 4/1986 | Schave et al. | 356/237.2 |
| 4,647,197 A | 3/1987 | Kitaya et al. | |
| 4,776,692 A | 10/1988 | Kalawsky | 356/239 |
| 4,853,777 A | 8/1989 | Hupp | 358/107 |
| 5,016,099 A * | 5/1991 | Bongardt et al. | 348/128 |

(Continued)

FOREIGN PATENT DOCUMENTS

JP 03-072206 * 3/1991

(Continued)

OTHER PUBLICATIONS

"Roller Wave Distortion—Definition, Causes and a Novel Approach to Accurate, On-line Measurement," Abbott et al., Glass Processing Days Conference Proceedings, Jun. 2002, 7 pages.

(Continued)

*Primary Examiner*—Tung Vo
(74) *Attorney, Agent, or Firm*—Edward Weck; Alan Kamrath

(57) ABSTRACT

A method and apparatus for detecting and measuring the optical distortion in pieces of glass and other reflective sheets are disclosed. The method inspects the full length and width of large area glass sheets or multiple sheets comprising a load of glass and uses optical magnification of a reflected circular image of precise size. A plurality of circular images is projected onto the glass and reflect as ellipsoids representative of local surface contours. The major and minor axes of the reflected axis define the axis of greatest magnification and demagnification. Distortions in the glass surface are measured in lens power as localized magnification at the elliptical axis. The angle and magnitude of the minor and major axis of the reflected ellipsoids provide data to map the surface profile of the glass. The method measures distortion of random or periodic frequency and measures distortion in all axes.

26 Claims, 10 Drawing Sheets

U.S. PATENT DOCUMENTS

| | | | | |
|---|---|---|---|---|
| 5,128,550 | A | | 7/1992 | Erbeck ........................ 250/572 |
| 5,138,268 | A | | 8/1992 | Mulkey et al. .............. 324/671 |
| 5,251,010 | A | * | 10/1993 | Maltby, Jr. ................... 356/613 |
| 5,459,330 | A | * | 10/1995 | Venaille et al. ......... 250/559.45 |
| 5,471,307 | A | | 11/1995 | Koliopoulos et al. ........ 356/371 |
| 5,602,648 | A | * | 2/1997 | Guering et al. .............. 356/445 |
| 5,724,140 | A | | 3/1998 | Haywood .................... 356/371 |
| 5,726,749 | A | * | 3/1998 | Schave ..................... 356/239.1 |
| 5,790,247 | A | * | 8/1998 | Henley et al. ............ 356/237.1 |
| 5,880,843 | A | * | 3/1999 | Hermosillo-Valadez et al. . 356/600 |
| 5,887,077 | A | * | 3/1999 | Bongardt et al. ............ 382/149 |
| 6,023,333 | A | | 2/2000 | Laux et al. .................. 356/371 |
| 6,437,357 | B1 | * | 8/2002 | Weiss et al. .............. 250/559.4 |
| 6,766,046 | B1 | * | 7/2004 | Saito et al. .................. 382/141 |
| 6,909,502 | B2 | | 6/2005 | Capaldo et al. ........... 356/239.2 |
| 6,980,291 | B2 | * | 12/2005 | Saito ........................ 356/237.2 |
| 6,985,231 | B2 | | 1/2006 | Redner |

FOREIGN PATENT DOCUMENTS

| | | |
|---|---|---|
| WO | WO 02/18980 A2 | 8/2001 |
| WO | WO 02/18980 A3 | 8/2001 |

OTHER PUBLICATIONS

"LiteSentry™ Real-time visual inspection systems for detecting Tempering Line Roller-Wave," Apr. 2000, 2 pages.

"LiteSentry™ On-line visual inspection systems for Measurement of Roller Wave Distortion," Nov. 2000, 2 pages.

Photograph, Jul. 2000, 1 page.

* cited by examiner

OPTICAL SYSTEM FOR IMAGING DISTORTIONS IN MOVING REFLECTIVE SHEETS

CLAIM FOR PRIORITY UNDER 35 U.S.C. §120

This is a continuation-in-part application of application number PCT/US01/27280 filed Aug. 30, 2001 which was published in English under PCT Article 21(2), which application claims priority on U.S. Application Ser. No. 60/230,281, filed Sep. 1, 2000.

FIELD OF THE INVENTION

The present invention relates generally to optical devices, and in particular a method and apparatus for measuring optical distortion in a reflective sheet.

BACKGROUND

This invention relates to an optical system for imaging distortions in a moving reflective sheet, such as distortions in glass sheets caused during a tempering process.

When glass sheets are tempered or annealed, they are transported through a heated furnace where they are heated to a critical temperature at which internal stresses are relieved. Achieving the critical temperature in a uniform manner over many square meters is difficult without softening the glass. Typically the glass reaches a softening point at which the glass is in a taffy-like state. The glass is transported on heat-resistant ceramic rollers, and gravity causes the softened glass to distort. Typical distortion is caused by sag in the glass between the rollers. If the furnace temperature is too high, sag can be pronounced. The sag is often cyclical in nature. The period of high points versus low points is related to a number of phenomena, two of which are the distance between adjacent rollers and the concentricity of the rollers. As an out-of-round roller turns, it imparts an imprint of periodic high points in the glass relative to its circumference.

When a glass sheet is conveyed out of the furnace, quenched, finished and ultimately installed in a building, the distortions due to tempering are noticeably visible. Beyond some tolerable level, such distortions are considered unacceptable, and the finished windows are rejected. When this occurs, the fabricator must replace the glass or the complete window unit.

The distortions caused by sag between the rollers or by an out-of-round roller tend to be cyclic in nature and to produce a corrugation effect in the glass sheet. These corrugation distortions are commonly known as roller wave distortions. All tempered or annealed glass has some roller wave distortion. While the glass industry quality standards specify an allowable peak-to-valley roller wave measurement, it has been difficult to accurately or easily measure roller wave distortion on the factory floor. Physical measurements are generally limited to only a small sample, due to the time required to measure with a dial indicator gauge. These physical measurements tend to be operator dependent with poor repeatability and are prone to error. Such tests may be destructive, often scratching the surface of the glass as the dial indicator gauge is rolled over the surface.

More commonly than physical measurement, an operator visually makes on-line measurements with a zebra board.

A zebra board consists of a large white backboard with black stripes painted diagonally across the board. As the glass sheets exit the quench area of the furnace, an operator views an oblique reflection of the zebra pattern in the glass as it moves on the conveyor. Roller wave distortions cause the straight diagonal lines of the zebra board to appear wavy in reflection. The more pronounced the roller wave, the wavier the lines appear. Operators are trained to judge the quality of the glass sheets subjectively, based upon the reflected image.

While helpful and inexpensive, a zebra board has limited use as a quality control tool. Customers are demanding improved and quantifiable quality in tempered glass products. Operators vary in their quality judgments, and consistent quality control is therefore difficult to achieve. There is no way to consistently quantify and document the results. Operators with the tasks of labeling, sorting and unloading glass have limited time for roller wave inspection.

When a glass sheet is fabricated and installed in a building window, an automobile, or a mirror, local distortions attributable to tempering or annealing may be noticeably visible. The visibly distorted areas of the glass act as lenses, bending the light in reflection and transmission, causing the light rays to displace and distort either reflected or transmitted images. Optical distortion is considered unacceptable beyond tolerable thresholds.

The glass industry has typically limited measurement of distortion to small samples in two dimensions, depth (z) and length in the direction of travel (y). Using a simplifying assumption that distortion is primarily a function of the rollers in the heat-treatment equipment, the industry has limited measurements to address roll wave or corrugation in the glass. Roll wave is described as long troughs and peaks parallel to the ceramic transport rollers, and is cyclical in period. Although roll wave distortion is problematic, local distortion across the glass in directions perpendicular to the transport rollers (x) is also highly problematic. This distortion is sometimes referred to as pocket distortion and is described as local point peaks and point valleys. Other distortion is referred to as micro corrugation and is described as corrugation in the glass at various angles due to draw lines or pullers used to spread the glass. No practical means exist for measuring these various distortions on a production line.

Current measurement means are limited to measurement of very small samples of glass relative to the volume of glass manufactured on the lines. Three such measurement means are flat bottom gauges, zebra boards (as described above) and interferometers. A flat bottom gauge with a dial indicator is used to measure gross peak-to-valley corrugation. Measurements are limited to a small sample, due to the time required to extract a sample from the process and measure with a dial indicator depth gauge over the entire surface of the glass. The sample is placed on a precision flat surface. Instrumentation is operator dependent with poor repeatability and is prone to error. Such tests may be destructive, often scratching the surface of the glass as the dial indicator gauge is rolled over the surface. The dial indicator is not able to measure pocket distortion or micro corrugation due to lack of resolution.

Further, the dial indicator depth gauge measures only one of the two parameters necessary to correlate the physical distortion to the optical distortion. Optical lens power is measured in diopters. Lens power (diopters)=1/f, where f is the focal length of the glass in the local region. $1/f=1/2R$ where R is the radius of curvature of the glass in the local region. The dial indicator makes an incorrect simplifying assumption that local distortion in glass is of constant radius of curvature, R. In fact, the radius of curvature of a local distortion is entirely dependent on local conditions during cooling and is infinitely variable.

Finally, interferometric measurements involve removing a strip of glass approximately 1 meter long by the full width of the float line. The sample is cooled, cut into 100 mm square samples and measured using interference fringe patterns through an interferometer. The method is highly accurate but destructive, and impractical for measuring glass from a float or tempering line. Three persons are required to measure less than 0.1 percent of the glass produced.

None of the methods in use is able to measure pocket distortion. Pocket distortion is physically too shallow to be measured using a dial indicator depth gauge, to random to be measured using interferometry, and not able to be quantified using a zebra board.

Customers of glass products demand ever-improved optical quality. Operators vary in their quality judgments, and consistent quality control is difficult to achieve. There is no practical means to consistently measure, quantify and document distortion in large volumes of glass. There is no practical means to measure pocket distortion and micro corrugation on a production line in real time.

Several automatic measurement systems have been proposed to solve this problem. U.S. Pat. No. 4,585,343 discloses a measurement apparatus for detecting and measuring roller wave distortions in sheet glass. This patent teaches a method of measuring a reflected pattern and comparing it to a control image. The preferred embodiment uses a plurality of complex optical systems, each of which requires precise alignment. The patent teaches a light pattern of 1×5¾ inch geometry changes as it is reflected from a concave versus a convex surface. It assumes the distortion in the glass is limited to uniform corrugation transverse to the direction of travel. The method collects a small sample of information in two dimensions, Y and Z.

U.S. Pat. No. 4,647,197 discloses a measurement apparatus using a CCD camera to detect a zebra board pattern transmitted through a windscreen. The pattern from a sample is recorded and compared to a reference pattern to quantify the quality of the sample.

U.S. Pat. No. 5,251,010 discloses a device for measuring roller wave using two parallel beams of monochromatic light. The preferred embodiment is limited to measuring one narrow strip of glass from a tempering furnace. As with U.S. Pat. No. 4,585,343, the device is limited to measuring corrugation in Y and Z directions and relies on the simplifying assumption that the glass is uniformly corrugated transverse to the direction of travel.

U.S. Pat. No. 5,726,749 discloses an apparatus for measuring distortion in curved windscreens using the angular deviation in a plurality of collimated light sources and an equally plurality of receivers, all precisely aligned. The method requires transmission of light through the glass and is directed at measuring distortion due to wedge variation and curvature variation in a laminated automotive windscreen.

Accordingly, there is a need for an improved optical detection apparatus for imaging and measuring optical distortions in reflective sheets.

BRIEF SUMMARY

The preferred embodiments described below include an optical system for imaging distortion of moving reflective sheets. The disclosed system includes a conveyor having a transport direction and a width transverse to the transport direction. This conveyor transports reflective sheets along the transport direction, such as glass sheets as they emerge from a tempering oven. A light source is mounted on a first side of the conveyor, and this light source is constructed to direct at least one continuous stripe across at least 90% of the width of the conveyor. One or more cameras are mounted on the first side of the conveyor and are oriented to detect two edges of a reflection of at least one of the stripes over at least 90% of the width of the conveyor. Each camera develops an output signal that is indicative of the separation between leading and trailing edges of at least one reflected stripe at a plurality of positions spaced along the width of the conveyor. The output signals are applied to a processor that uses the captured image of the reflected stripe to identify lateral edges of glass sheets on the conveyor. The processor then uses the separation between the detected leading and trailing edges of the stripe to assess distortion, including roller wave distortion.

The system described below allows the full surface area of each glass sheet to be monitored for distortion, regardless of the size of individual glass sheets, the number of glass sheets placed side by side on the conveyor, or the location of glass sheets on the conveyor. This represents a substantial improvement over the prior-art automatic measuring systems, because tempering oven conveyors are typically loaded with glass sheets that differ in size and position on the conveyor.

An optical apparatus for measuring lens power of optical distortion of reflective sheets is also disclosed. The disclosed apparatus comprises a conveyor having a transport direction (y) and a width (x) transverse to the transport direction. This conveyor transports reflective sheets, such as glass sheets, along the transport direction as they emerge from a heat treatment process. A light source is mounted on a first side of the conveyor, and this light source is constructed to direct a pattern of white circles on a black background over the entire width of the glass conveyor. One or more cameras are mounted on either side of the conveyor and are oriented to detect the reflected (or transmitted) images and measure the magnification of each. According to one aspect of the invention, the incident image spans the entire width of the conveyor, then measures lens power in both X and Y dimensions over the entire area of the sheets. The apparatus described allows the full surface area of each glass sheet to be measured for lens power, regardless of the size of individual glass sheets, the number of glass sheets placed side by side on the conveyor, or the location of glass sheets on the conveyor. The apparatus described measures and quantifies distortion over the entire surface of large glass sheets. The apparatus quantifies and records distortion in lens power in real-time on a production line. Real-time measurement and feedback allows the glass manufacturer to control the heat treatment processes and thereby control the distortion to acceptable levels.

The foregoing summary has been provided by way of general introduction, and it is not intended to limit the scope of the following claims.

DETAILED DESCRIPTION OF THE PREFERRED EMBODIMENTS

General Discussion

Figure 1:
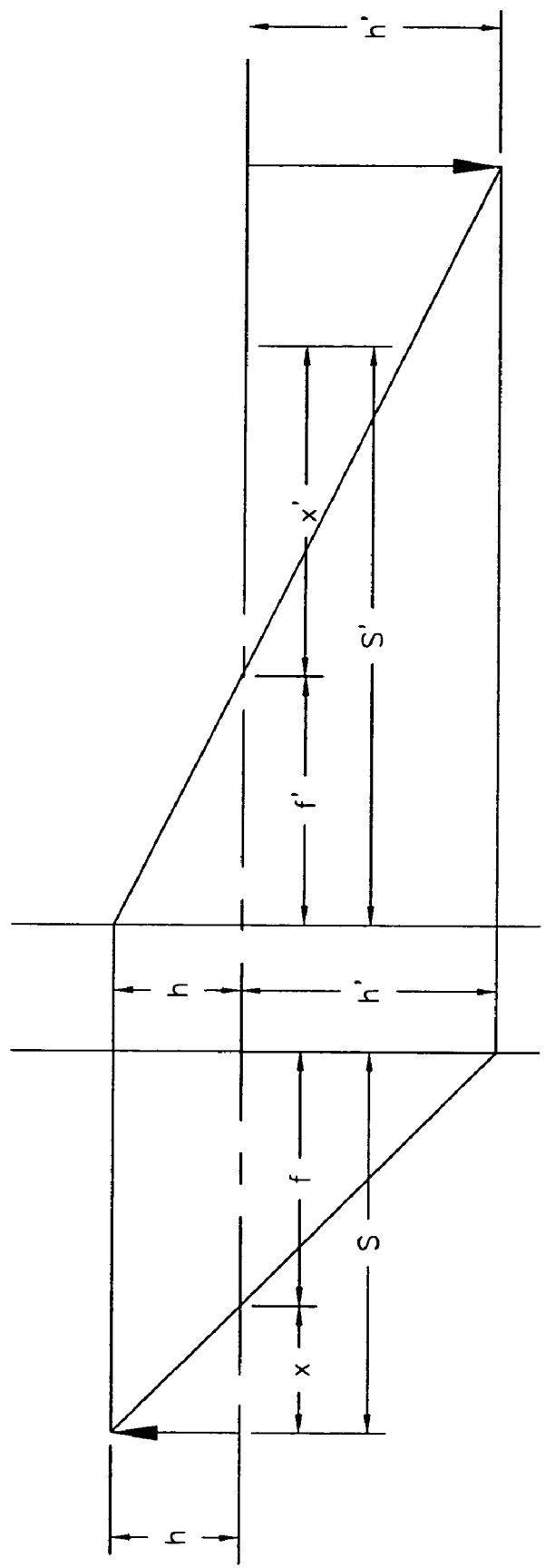
FIG. 1 shows a schematic illustrating the relationship between magnification and focal length in an optical detection apparatus.

The present invention provides an improved optical system for measuring cyclic roller wave distortion in sheet glass or other reflective substrates.

The improved roller wave measurement system described below includes a glass transport conveyor, a light source that patterns at least one light stripe across the width of the conveyor, a set of CCD cameras, and a computer system.

The glass transport conveyor is typically an existing conveyor section at the exit of the tempering equipment. This is an advantage of this system, because specially outfitted or precision conveyors are not required. Glass sheets ranging in size and quantity from single large sheets to multiple small sheets in a grid pattern on the conveyor are continuously transported out of the furnace to an unload area (or to additional process equipment). As used herein, the term "conveyor" is intended broadly to encompass the widest variety of devices for transporting reflective sheets, including roller-type conveyors, belt-type conveyors, and the like.

The light source is installed over the conveyor and is designed to pattern a stripe across the full width of the conveyor. The light source in this example includes a box constructed to contain fluorescent light bulbs in sufficient quantity to provide bright diffuse light. The bulbs are rated for high-frequency use, and electronic switching type ballasts are used to avoid 60 Hz beating with the camera video rate. The front of the light box is an opaque, black cover with a long translucent striped area extending the length of the box. The box length is matched to illuminate the full conveyor width. When the light stripes are reflected by passing glass sheets, the reflected image is seen by the CCD camera or cameras mounted over the conveyor. In view of the viewing angle of the camera or cameras, the light box is may be somewhat longer than the conveyor width, though this is not required.

To detect the reflected stripe images from glass sheets passing on the conveyor, an area array photo detector such as a digital CCD camera is used. As glass with roller wave distortions passes under the light source and camera, the light stripe reflections are optically altered by the cyclic, roller wave distortions. The reflected stripes appear to alternately become wider and narrower as the glass travels by. While this occurs, the camera records images and sends this data to the computer system. The computer system uses this data and calculates the changes in stripe width distance (measured along the transport direction) over the full area of each piece of glass. By looking at a sufficient number of data points, the cyclic wave of distortion is measured in the data and the roller wave distortion is determined.

The computer system includes a computer monitor that displays a simplified depiction of the conveyor section. After each load of glass passes under the light source and camera, a depiction of each sheet of glass is shown in a color representing the level of roller wave distortion found on that sheet. The average measured roller wave distortion for each depicted sheet is displayed at the center of the respective sheet. The data for each sheet and load is also stored for generating written reports, and a trend graph at the bottom of the monitor shows the load average roller wave distortion for the last 24 hours.

The present invention provides an optical apparatus for measuring optical distortion as measured in lens power over large areas of glass sheets or other reflective substrates. Distortion in a flat surface can be defined as local curvature in the otherwise flat surface, such as glass or any other reflective translucent material, such as acrylic. Lens power is measured using magnification of images as they reflect from localized distortions in the glass sheet. Lens power is the reciprocal of focal length. Focal length is related to optical magnification using the following equations.

$$S'=f(1-m)$$

$$S=f(1/m-1)$$

Where S' is the image distance from the principal lens plane, S is the object distance from the principal plane, f is the focal length of the lens, and m is the magnification of the lens, as shown for example in FIG. 1. As will be discussed in more detail in reference to later figures, the 'lens' in this case is the localized distortion in the glass sheet.

SPECIFIC EXAMPLE

Figure 2:
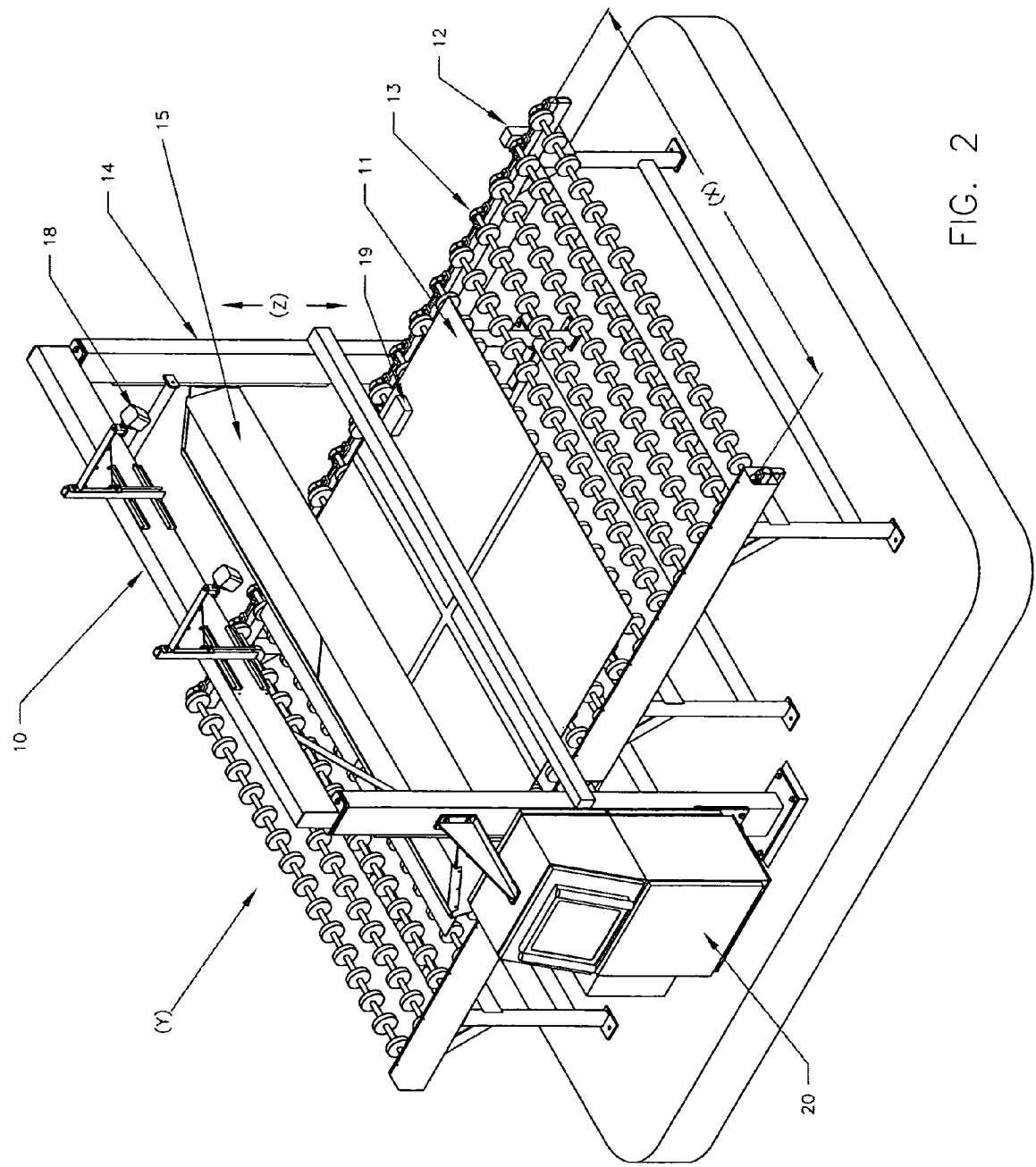
FIG. 2 shows an overview of a first embodiment of this invention in perspective view, showing a conveyor at the unload end of a glass heat-treating system.

Referring to FIG. 2, there is shown a perspective view of a roller wave measurement system 10 for use in inspecting individual glass sheets 11 which have been treated by a glass tempering system. In FIG. 2, the glass tempering system includes a conventional encoding device, 12 such as a rotary signal detector, detects the movement of the glass on the conveyor based upon the rotation of one of the rollers of a conveyor 13 having a plurality of rollers. The transport direction is indicated by the arrow T, and the conveyor width is indicated by the arrow W. As glass sheets 11 exit the tempering system, the apparatus 10 measures the roller wave distortion in the sheets 11. The apparatus includes a support frame 14 and a light box 15 having a set of light bulbs 16 and a patterned diffuser 17. The light bulbs 16 are high-intensity, high-frequency fluorescent tubular bulbs manufactured by Voltarc or similar, spanning the entire length of the light box 15. The light box 15 length exceeds the conveyor width W by a distance such that the image capture cameras receive reflections of light from the light box 15 over the entire width W. The light box is constructed of rigid steel such that deflection of the plane of the box over the conveyor 13 is minimized. The diffuser 17 is made of high transmission white acrylic sheet or similar polymer and is printed by a silk-screen process with a pattern of opaque lines on the translucent white background. The pattern can be a set of parallel stripes or an orthogonal pattern of parallel stripes and intersecting lines approximately 25 mm apart.

Figure 3:
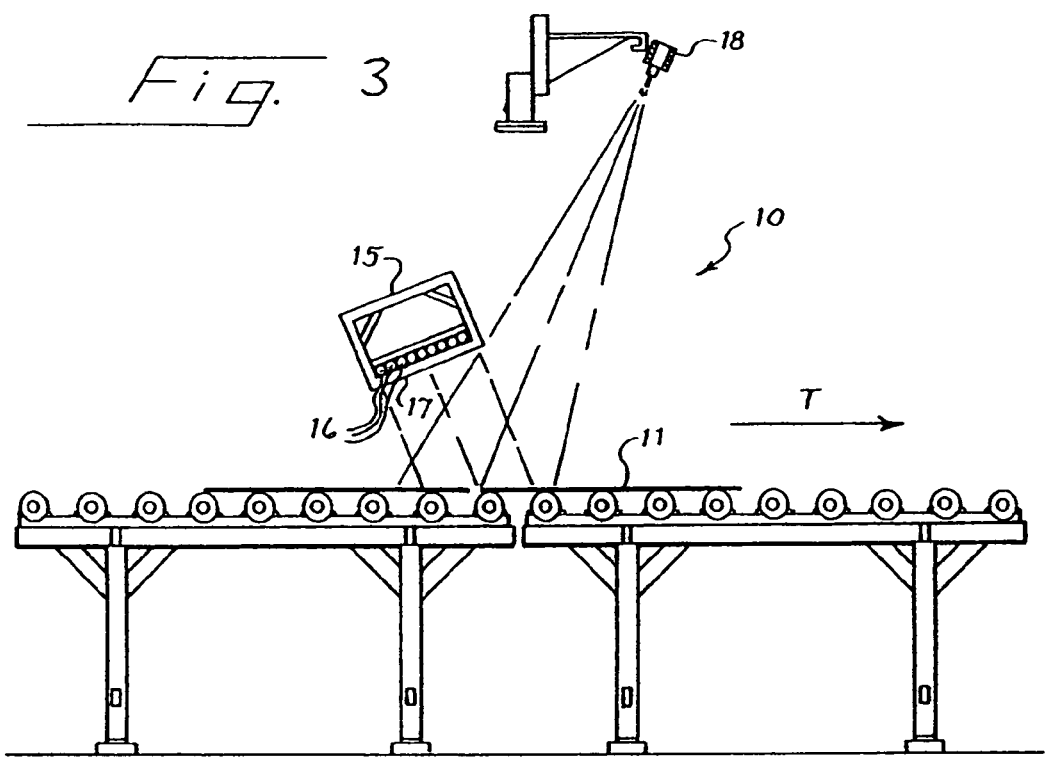
FIG. 3 shows a sectional side view of the conveyor and embodiment of FIG. 1, depicting the conveyor, substrate, light source and image capture device.

In FIG. 3, the glass sheets 11 are conveyed under the light box 15 and diffuser 17, and the patterned image is projected onto and reflected from the surfaces of the glass sheets 11. The reflected image is captured by the CCD cameras 18, which may each comprise an 8.5 mm lens and a photodiode array measuring 480×760 pixels or greater, manufactured by AccuSentry, Inc. As shown in FIG. 3, each camera 18 is preferably mounted farther from the conveyor 13 than is the diffuser 17. This approach reduces the length of the diffuser 17, and it reduces the viewing angle required of the camera 18, and thereby the fish-eye distortion.

The image capture CCD cameras 18 apply output signals to a high-speed processor 20 that executes algorithms to process the data. This processor 20 can be an Intel III, 550 MHz or faster microprocessor. A high-speed connection from the cameras 18 to the processor 20 is direct and requires no signal preprocessing or frame grabbing.

The image captured by the cameras 18 includes high-contrast black stripes on a white background. A thickness sensor 19 measures thickness of each load in real-time as it passes through the apparatus. Thickness information is sent to the computer 20. The algorithm executed by the processor 20 captures these high contrast stripes across the entire width W of the conveyor 13, allowing the processor 20 to differentiate between individual sheets of glass. As the glass moves under the system, images are captured, distances between two edges (e.g., between the leading and trailing edges of a stripe or between two leading edges or two trailing edges of different stripes) are measured, and the measured distances are compared to prior distance data. Maximum and minimum distances are defined and correlated to actual distortion in the glass sheets. This algorithm is implemented in real time without the need to compare the data to a known flat surface. Results are provided to the unload personnel as the glass arrives to be unloaded.

Figure 4:
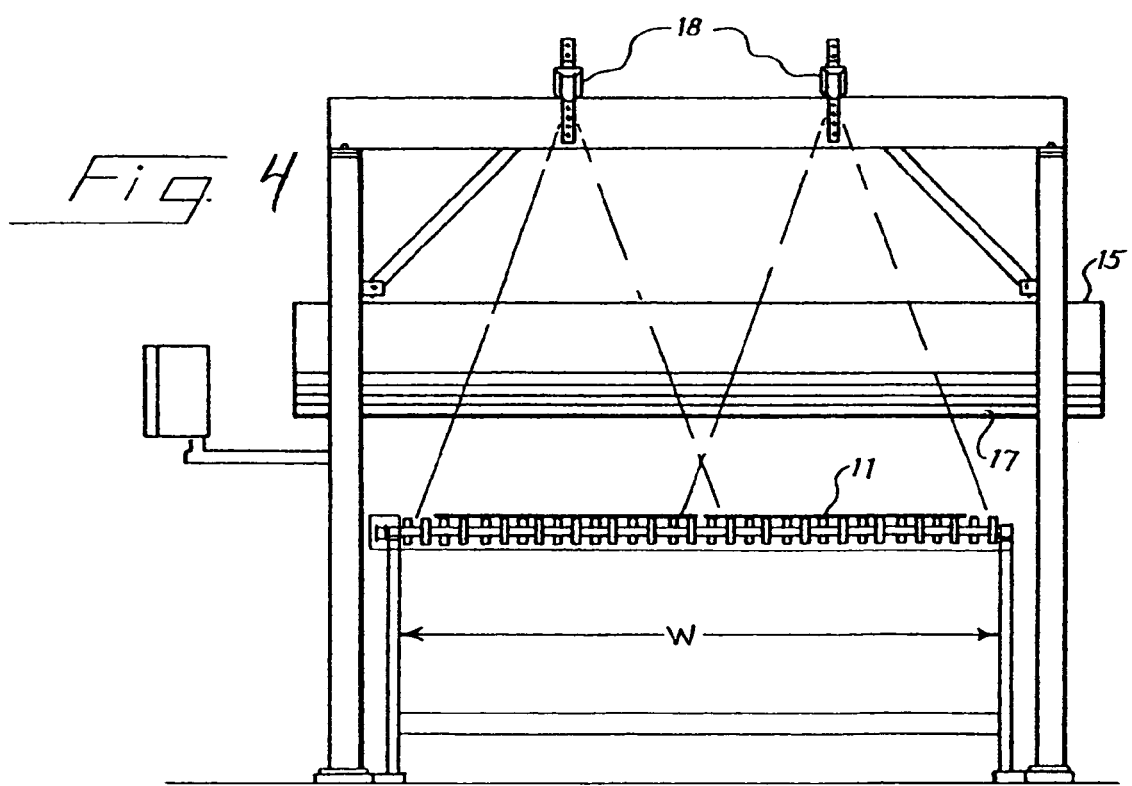
FIG. 4 shows an end view of the embodiment of FIG. 1, depicting the conveyor, substrate, light source with striped pattern, image capture devices and support frame.

FIGS. 5a-54c illustrate operation of the system described above. In these figures, the period of the roller wave distortion is indicated by the dimension P, and the stripe 22 on the diffuser 17 has a width equal to ¼P or ¾P. The image prior to reflection is shown as $I_P$, and the image after reflection is shown as $I_1$ in FIG. 4a (concave reflecting surface) and $I_2$ in FIG. 5b (convex reflecting surface). The widths of the reflected images $I_1$ and $I_2$ are $W_1$ and $W_2$, respectively, and $W_1 > W_2$. As the glass sheet 11 is moved in the transport direction T, the width of the reflected image of the stripe 22 cyclically varies between $W_1$ and $W_2$, and $W_1 - W_2$ is a measure of the amplitude of the roller wave distortion.

Figure 5A:
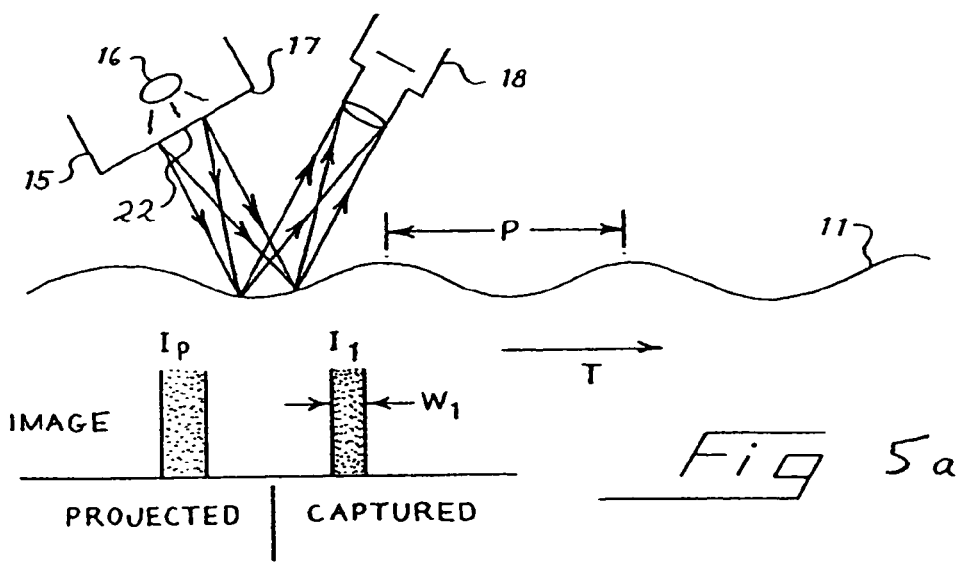
FIGS. 5a-5c are schematic views illustrating the manner in which a patterned image is projected onto a substrate with a cyclical distortion, reflected from said substrate and captured. These figures illustrate the change in the reflected pattern as the distortion changes in shape from concave to convex.
Figure 5B:
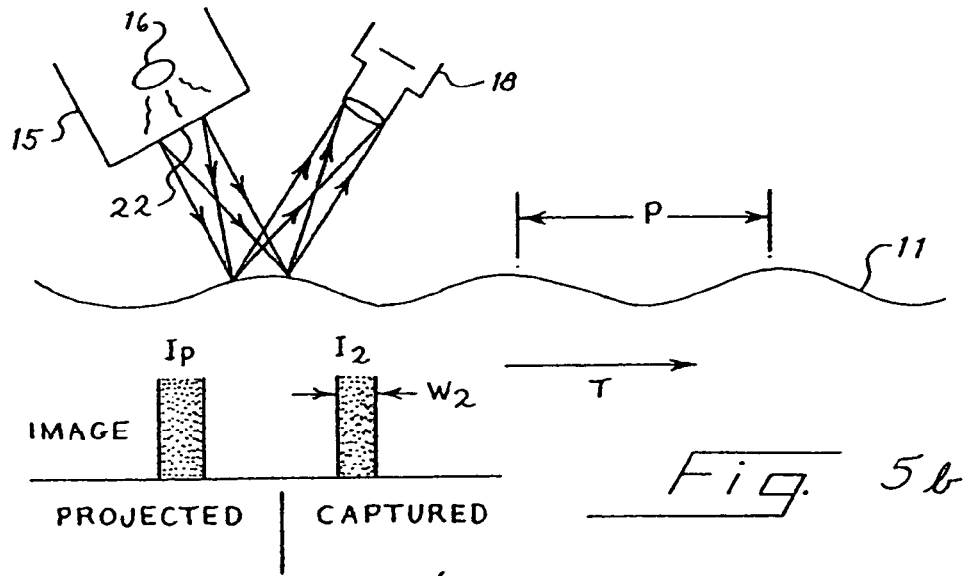
Figure 5C:
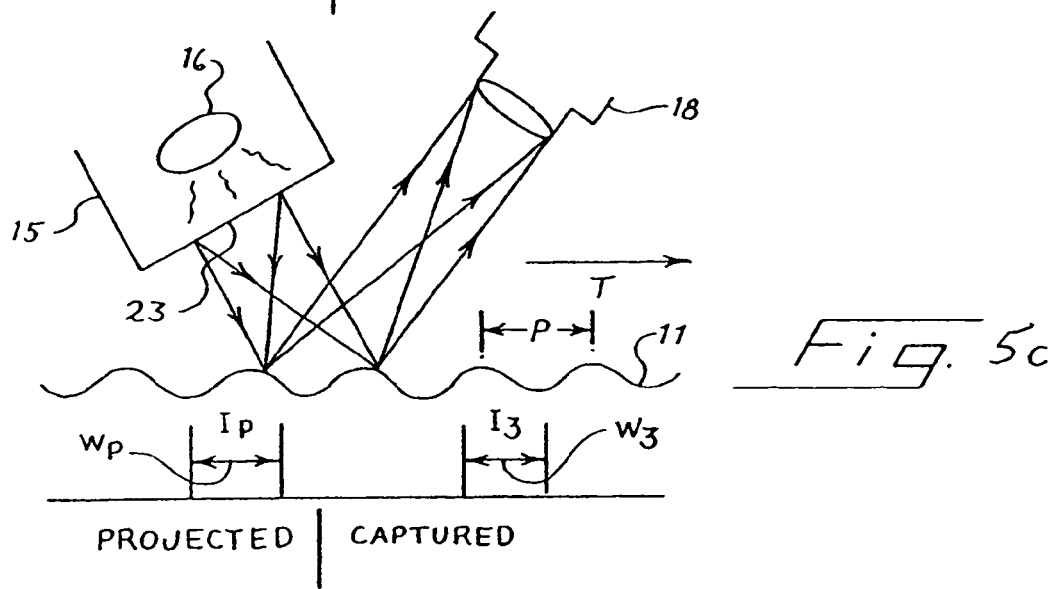

As shown in FIG. 5c, a stripe 23 with a width equal to P, is not well-suited to measuring roller wave distortion, because both the leading and trailing edges of the reflected image can be simultaneously situated at the peaks or the troughs of the roller wave.

Shave teaches in U.S. Pat. No. 4,585,343 that a light pattern of 1×5¾ inch geometry changes as it is reflected from a concave versus a convex surface. However, Shave teaches that the changes in geometry must be compared to a reference flat sheet of glass in order to arrive at a result. In the preferred embodiment, the projected stripe image spans the entire width of the conveyor and the leading and trailing edges of the stripe are spaced either ¼ or ¾ the length of a glass sheet distortion cycle (or any odd ¼ wavelength). When lines are included parallel to the transmit direction, the stripes and lines form an array of squares measuring about 1 inch by 1 inch. No comparison is needed to a known flat surface.

In the preferred embodiment, the light source is built to pattern at least three (preferably four) stripes across the width of the conveyor 13. Using at least three stripes, the processor 20 checks that a sheet of glass is reflecting all three stripes before taking measurements. When the distance between edges of the center stripe is measured, the processor can assure measurement of a stripe and not the edge of the glass sheet to one edge of the stripe.

This optical system and measurement technique described above have many advantages:

1. The system can be installed over an existing conveyor with minimal installation downtime. Once operating, the system makes roller wave distortion measurements on-line with responsive display of results to the operators. Operators do not have to visually judge distortion level and do not have to remove sheets for off-line testing.

2. A single light source and camera system is used to measure distortion over the entire area of each sheet. This significantly improves on earlier work by Schave (U.S. Pat. No. 4,585,343), which requires a plurality of complete optical systems including light sources and matching sensors. A plurality of such systems would be required to measure glass distortions in the sheet widths that are typically tempered, such as 48, 60, 84, 96 or greater inches. The present system uses a single light stripe source to inspect the entire width of the conveyor. In one preferred embodiment, one light source is used with two cameras. The cameras are synchronized, each detecting more than one half of the single reflected stripe. The simplicity of this arrangement improves reliability and minimizes maintenance and system cost.

3. Roller wave distortion is measured simultaneously for multiple glass sheets as they pass under the light source and camera. In typical sheet glass processing, conveyors are filled with loads comprising multiple sheets of varying sizes placed randomly on the conveyor. While one load may be a single large sheet covering the entire conveyor, the next may contain sixteen smaller sheets. The system described above is capable of measuring each individual sheet of glass and reporting on the roller wave distortion for each sheet. After a load has passed under the light source and camera system, a roller wave measurement is displayed for each sheet.

4. All sheets on the conveyor are measured. The full width of the conveyor is scanned continuously. This greatly improves on earlier systems that use a single monitoring point. Sheets may be placed in any configuration on the conveyor. There are no lanes which are monitored—or missed—by point measurement sensors. The continuous stripe image provides the data that enables the computer system to locate the lateral edges of individual glass sheets.

5. The system does not require calibration with a reference, non-distorted, flat glass sheet. An absolute measurement of roller wave distortion can be made. Operators are not required to calibrate the device periodically by interrupting production and placing reference sheets under the system.

6. Mounting and alignment of the light source and camera system are not critical. The use of a common, diffuse, white light source provides easy installation, operation and maintenance. The light bulbs may be commercially available florescent lights. While care should be taken to mount and focus the cameras on the stripe reflection in the glass, alignment by hand and eye is satisfactory. This improves on past systems using complex, costly laser optics requiring many components and exacting alignment.

7. Typical bouncing motion of the glass on the conveyor due to vibration does not adversely affect system accuracy. The system measures a relative absolute distance from peak to valley, not an actual position of the light stripe. Therefore movement of the reflected image of the stripe in the camera's field of view is inconsequential. The width of the reflected image of the stripe depends only on the initial stripe width and the distortion effect of passing glass. As long as the stripe to be measured remains in the camera's field of view, the system functions.

Further Considerations

Figure 6:
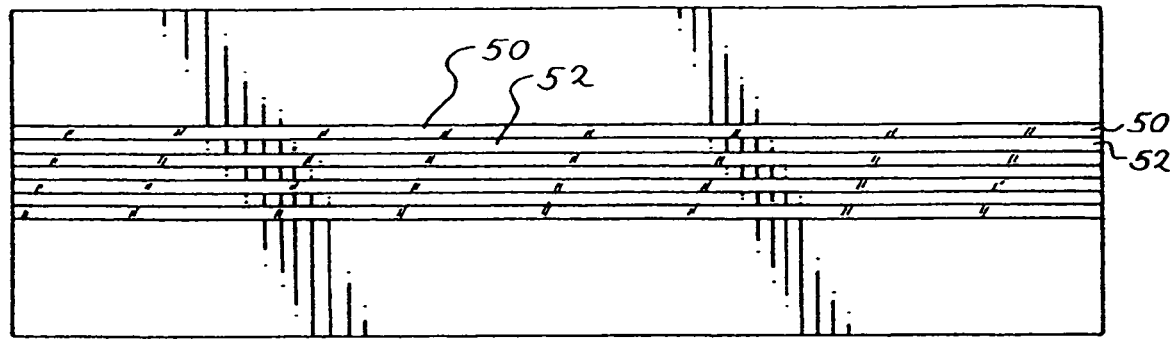
FIG. 6 is a plan view of a diffuser suitable for use in the embodiment of FIG. 2.

FIG. 6 shows a plan view of a diffuser 10 that can be used with this invention. As shown in FIG. 6, the diffuser 10 is generally opaque, and it defines four spaced, parallel transparent regions 50. The transparent regions 50 are separated by opaque regions 52. In this example, the transparent stripes 50 are each 0.75 inches in width, and the intervening opaque regions 52 are each 0.50 inches in width.

Figure 6A:
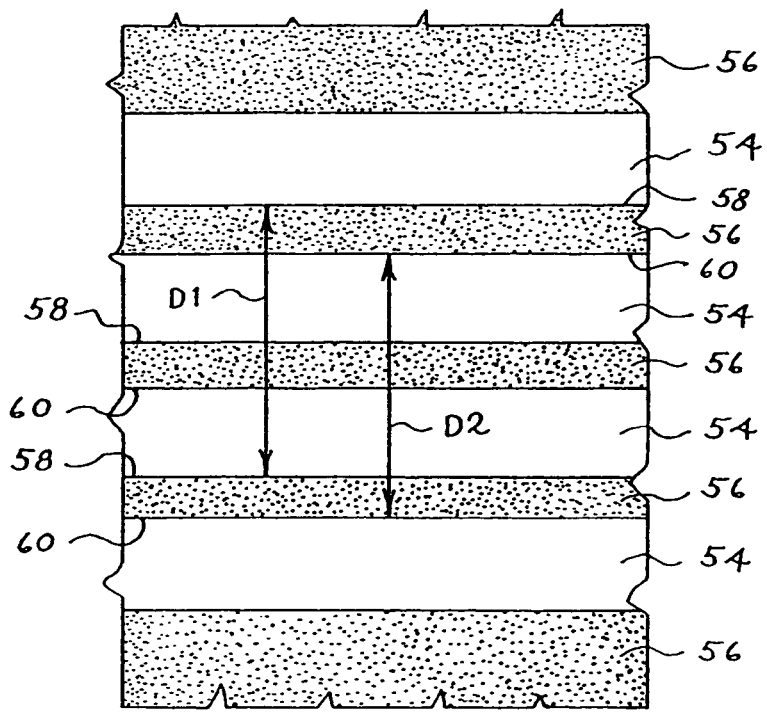
FIG. 6a is a fragmentary view of a reflected image captured by the system of FIG. 2.

FIG. 6a shows a resulting reflection as recorded by the camera 18 discussed above. In FIG. 6a, the bright regions 54 of the image correspond to the reflected stripes, and the dark regions 56 of the image correspond to image to dark portions of the reflection of the diffuser. The image of FIG. 5a provided sharp edges 58 between adjacent light regions 54 and dark regions 56.

Preferably, the high speed processor 20 measures distances between two separate pairs of edges from each exposure recorded by the camera. In FIG. 6a, the distance D1 and the distance D2 are examples of two such measurements. Preferably, such measurements are made at a precise distance apart, 0.5 inches along the length of the stripe in the preferred embodiment. Distances D1 and D2 are repeatedly measured and compared to previous measurements from other exposures. The benefit of using two pairs of edges for measurement is that twice as much data is collected with each exposure. Exposure time and light intensity constraints are reduced, and collecting two or more data sets with each exposure optimizes exposure time, light intensity and processor use.

Figure 7A:
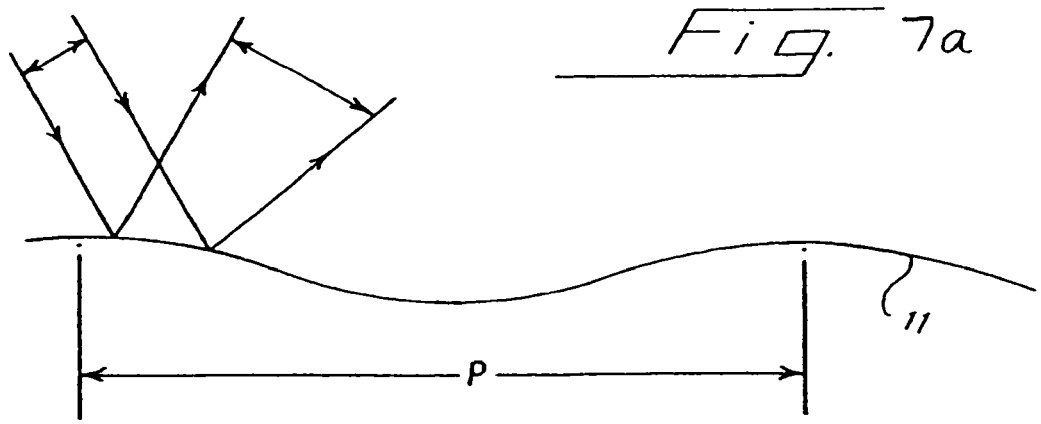
FIGS. 7a and 7b are schematic views illustrating the manner in which a patterned image is distorted by convex and concave surfaces, respectively.
Figure 7B:
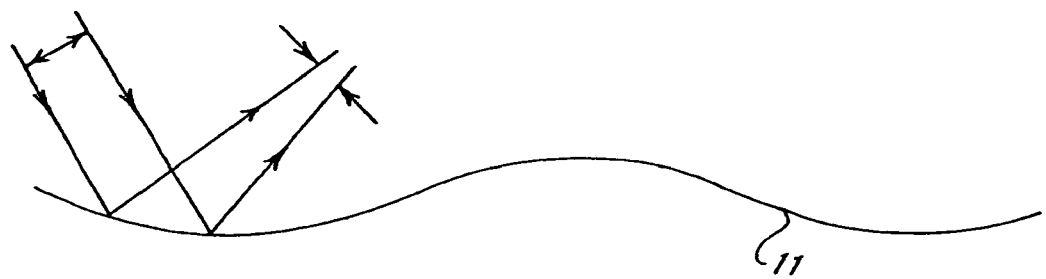

FIGS. 7a and 7b provide further information regarding the optical distortions measured by the system described above. For a flat surface, reflections of the stripes described above are not distorted and the rays at the stripe edges remain parallel on incidence and on reflection. FIG. 7a shows the situation where a pair of stripe edges are reflected off of a convex portion of the glass surface. For a convex reflecting surface, one or both of the angles of incidence increase (as compared to a flat reflecting surface), the angles of incidence for the two rays are not equal, and the reflected rays diverge. This increases the distance between the selected stripe edges as recorded by the camera (as compared to a reflection off of a flat surface). FIG. 7b shows the situation where a pair of stripe edges are reflected off of a concave surface of the glass sheet. For a concave reflecting surface, one or both of the angles of incidence decrease (as compared to a flat reflecting surface), the angles of incidence of the two rays are not equal, and the reflected rays converge. This decreases the distance between the selected stripe edges as recorded by the camera (as compared to a reflection off of a flat surface).

In general, the period P of the roll wave can vary, though it generally ranges from 4-12 inches. If the value of P were known, the preferred measured width would be ½ P. The current preferred embodiment measures distances between pairs of edges that are separated by about 2.5 inches, which results in an edge separation between about ¼ P and ⅝ P. In general, any stripe with less than the smallest expected value of P can be used, and the preferred values discussed above should not be considered limiting.

Empirical evidence shows that multiple superimposed wave periods are often evident in the surface of the heat-treated glass sheet. The problem of properly assessing distortion resulting from wave periods that vary and include multiple separate periods can be addressed using the system shown in FIG. 8. This system includes a conveyor 13 for glass sheets 11 and a camera 18, all as discussed above. In this example, a motion monitor 70 is coupled to the conveyor 13 to produce a trigger signal that defines the sampling or measurement period. Because the motion monitor 70 is responsive to conveyor motion, the trigger signal can be generated at every fixed increment of axial travel of the glass sheet 11. For example, the motion monitor 70 can be implemented as an optical encoder mounted to one of the rolls of the conveyor under the observation station. The encoder tracks movement of the substrate in the direction of travel, and it triggers the camera 18 to store images of the reflected stripes at precise intervals of movement. For example, the trigger signal can trigger the camera 18 to store an image of the reflected stripes at positions of the glass sheet separated by 0.5 inches of travel of the glass sheet 11.

Figure 8:
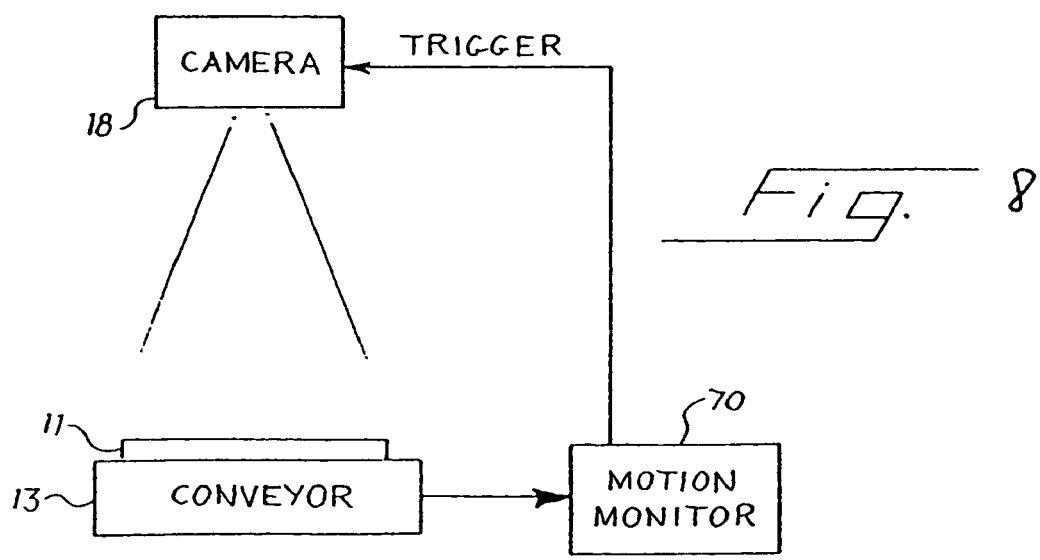
FIG. 8 is a block diagram representation of selected components of a modified version of the system of FIG. 1.
Figure 9:
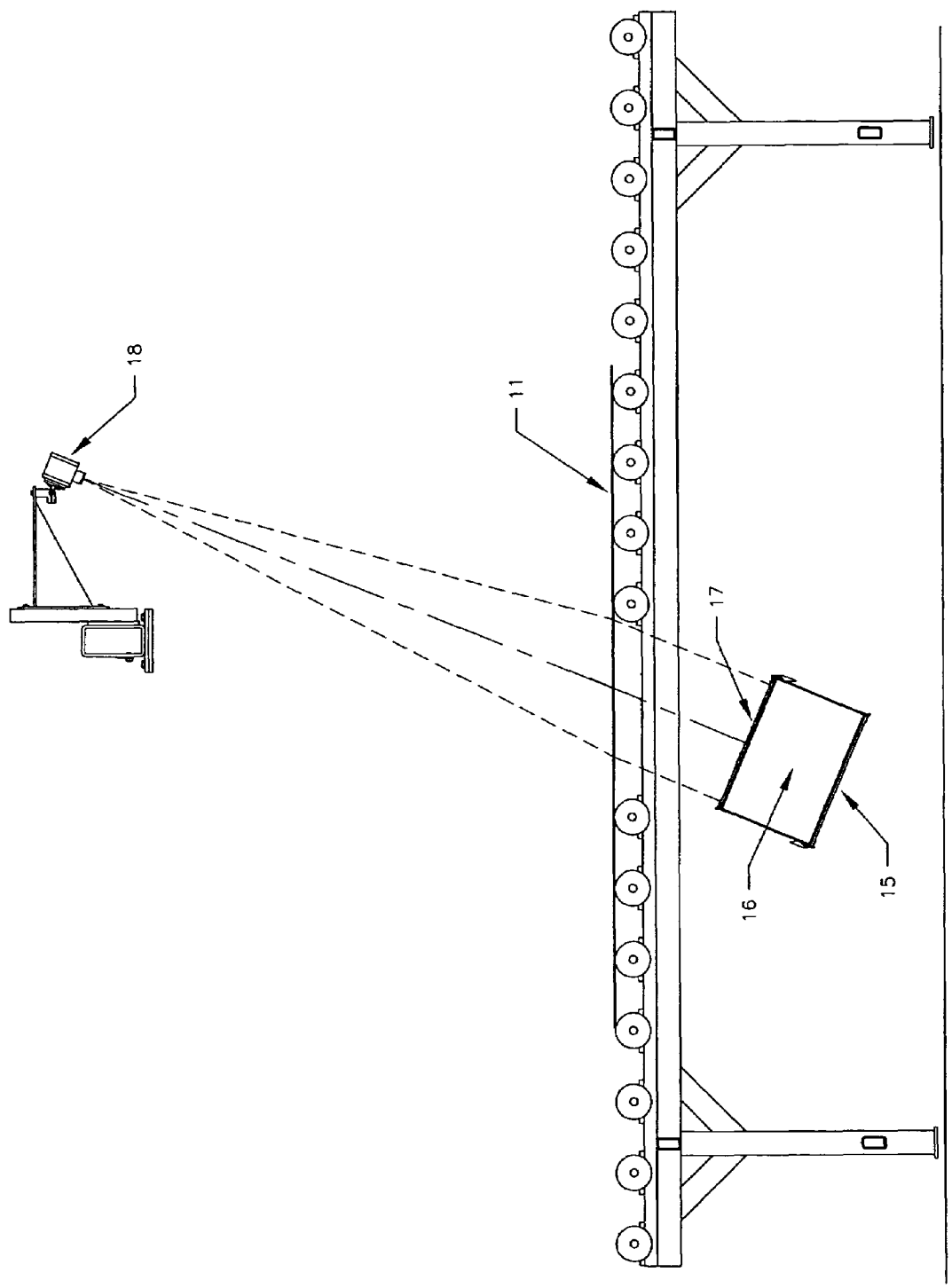
FIG. 9 shows a sectional side view of an apparatus for measuring optical distortion according to an alternate embodiment.

The system of FIG. 8 provides precisely spaced sampling. The distance between selected stripe edges can be measured as described above, and these distances can then be subjected to a Fourier transform analysis. The results can include surface typography and the measurement of lens power in diopters. Diopter measure is an absolute measurement of optical distortion in the finished product and eliminates the dependence of an assumed period P based on furnace or roll circumference or other periodic disturbance.

Simply by way of example, the camera 18 may be implemented as a CCD camera of the type supplied by AccuSentry as model AS-9000. The camera may use an 8 mm lens, and the motion monitor 70 can be implemented as an optical encoder of a type supplied by Heidenhain as a type 529/2013.05000 encoder. The camera sampling period is approximately 0.5 inches of travel of the glass sheet in this preferred embodiment or ⅛ to ³⁄₆₄ of the expected roll wave period. The sampling period should be less than ½ of the shortest expected value of P to avoid aliasing.

CONCLUDING REMARKS

Of course, many alternatives are possible to the preferred embodiment described above. The light source can take any suitable form, and it can if desired use slits (without the diffuser described above) to form one or more stripes extending across substantially the entire width of the conveyor. Alternatively, the light source may include a patterned opaque object that is externally illuminated rather than the internally illuminated light box described above. In yet other alternatives one or more scanned laser beams can be used to form one or more continuous stripes across the conveyor width.

The term "stripe" is intended to mean an image having a leading edge and a trailing edge in the transport direction. A stripe may or may not have intervening features between the leading and trailing edges. The pattern of stripes across the width of the conveyor can vary widely. Each stripe may be either defined by light presence or absence, in any desired wavelength or band of wavelengths. Though each stripe is preferably a straight, parallel-sided stripe oriented transverse to the transport direction, various nonparallel-sided stripes, or curved stripes, can be used, in sets of one, two, three or more stripes. As explained above, lines oriented parallel to the transport direction may be formed to intersect the stripes.

Though the preferred stripes described above extend across the entire width of the conveyor, in alternative embodiments the stripes may not extend entirely to the extreme edges of the conveyor. For example, in one alternative embodiment, the continuous stripe extends across at least 90% of the width of the conveyor. This still allows the computer system to detect lateral edges of glass sheets on the conveyor, which appear in the reflected image as interruptions in the reflected stripe.

As another alternative, the stripes may be skewed with respect to the transport direction. The preferred arrangement, in which the stripe is transverse to the transport direction, simplifies optical design and calculations performed by the computer system.

A wide variety of cameras can be used to detect the reflected image of the stripe or stripes. As used herein, the term "camera" is intended broadly to encompass any system for generating an output signal that is indicative of the imaged stripe reflections, including at least two edges of at least one of the stripes.

The term "set" is intended broadly to mean one or more.

The apparatus according to an alternate embodiment of the present invention and accompanying software measure and calculate the minor axis, the major axis, the major axis angle and other geometric attributes of each ellipsoid. The image capture and measurement requires less than 50 ms for several hundred ellipsoids. Using precise measurement of the major and minor axis of the localized distortion, analysis is made.

If both major and minor axes are less than nominal diameter as measured on the particular thickness of flat glass, the local distortion creates a reflected ellipsoid which is a demagnified version of the image, and the local surface is convex. If both axes are greater than the nominal diameter for the thickness of glass being measured, the local distortion creates a reflected ellipsoid which is a magnified version of the image and the local surface is concave. If one axis is greater than the nominal diameter and one axis is less than the nominal diameter, then the local contour is in transition and the greatest difference from minimal is used to define local contour.

The apparatus according to an alternate embodiment of the present invention preferably includes a glass transport conveyor, a light source that patterns a plurality of circular images across the width of the conveyor, a set of CCD cameras, a thickness sensor to measure the thickness of each sheet, and complementary high speed computers. The thickness sensor could be, for example, a conventional laser detector to detect a reflected laser beam from both sides of a glass sheet to determine the thickness of the sheet. Although light waves and corresponding cameras used to detect reflected images are described, any signal and corresponding detector could be used according to the present invention.

The glass transport conveyor could be an existing conveyor section at the exit of the tempering equipment for example. An advantage of the apparatus of the present invention is that specially outfitted or precision conveyors are not required. Glass sheets ranging in size and quantity from single large sheets to multiple small sheets in a grid pattern on the conveyor are continuously transported out of the heat treatment apparatus to an unload area (or to additional process equipment). As used herein, the term "conveyor" is intended broadly to encompass the widest variety of devices for transporting reflective sheets, including roller-type conveyors, belt-type conveyors, and the like.

The light source is installed over the conveyor and is designed to project a pattern of images such as circles across the full width of the conveyor. The light source could include a box constructed to contain fluorescent light bulbs in sufficient quantity to provide bright diffuse light. The bulbs are preferably rated for high-frequency use, and electronic switching type ballasts are used to avoid 60 Hz synchronization with the camera video rate. The front of the light box is an opaque, black cover with a pattern of translucent image areas extending the length of the box. For example, the translucent image areas comprise image areas formed in a translucent material such as an acrylic material to create a diffused light source. The light box length preferably exceeds the conveyor width by a distance such that the view angle of the imaging lens captures the reflected image over the entire width of the glass sheet. When the projected circles are reflected from the glass sheets passing below, the reflected image is seen by the CCD camera or and array of cameras mounted over the conveyor. Alternatively, the image could be projected onto the reflective substrate using a point light source and reticle to form the image.

Figure 10:
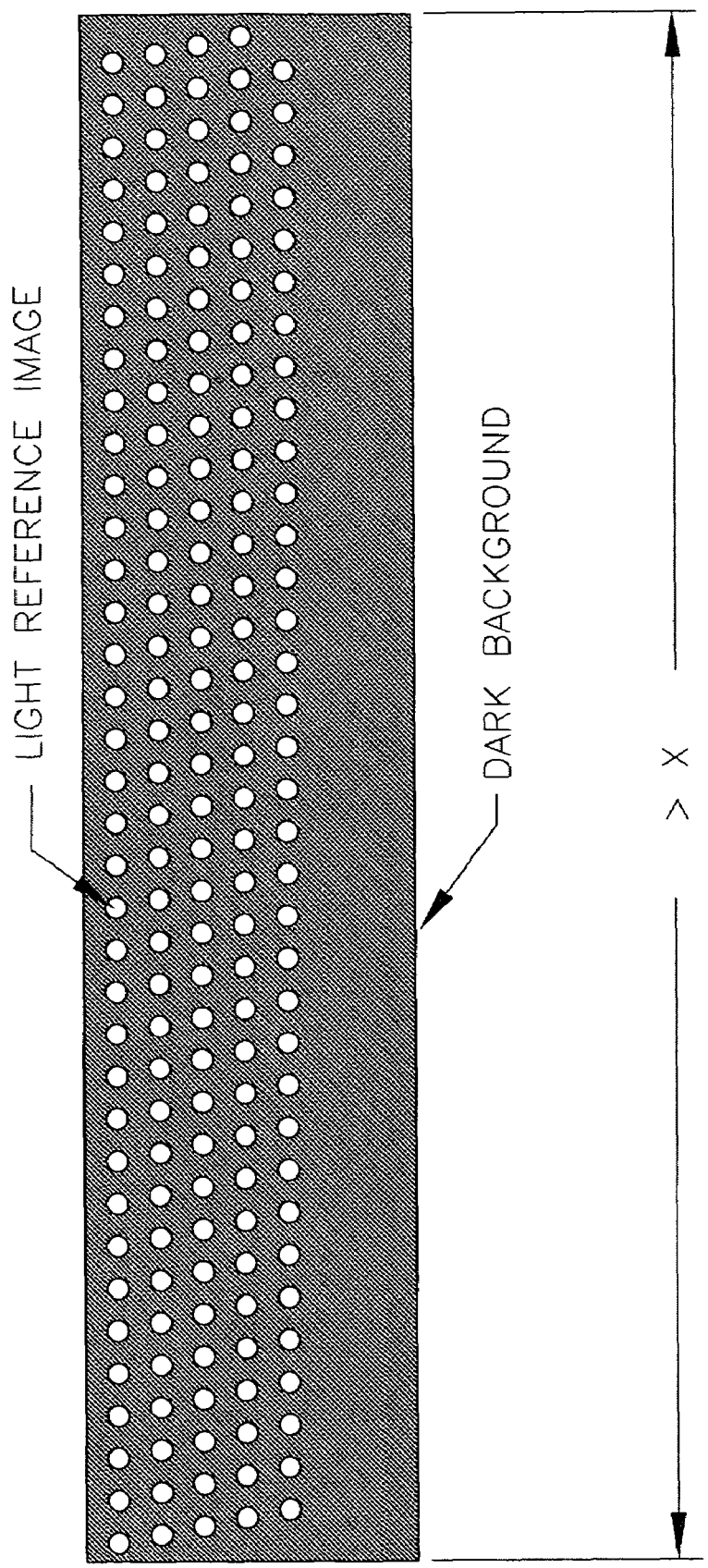
FIG. 10 shows an incident image for projection onto the glass according to the present invention.

According to an alternate embodiment of the present invention projecting an incident image according to FIG. 10, the glass sheets 11 are conveyed under the light box 15 and diffuser 17, and the patterned image is projected onto and reflected from the surfaces of the glass sheets 11. The light source 16 is preferably high-output T5 fluorescent tubular bulbs, such as bulbs manufactured by Sylvania or similar, spanning the entire length of the light box 15. The diffuser 17 is preferably made of high transmission white acrylic sheet or similar polymer and is printed with a pattern leaving circles on an opaque background. The pattern could be made on a precision plotter. The reflected image is captured by the CCD cameras 18. Alternatively, the light source could be positioned on the opposite side of the glass sheet, as shown for example in FIG. 9, whereby the camera would detect the transmitted light. The CCD cameras may each comprise a 12.5 mm lens and a photodiode array measuring 1004×1004 pixels or greater, manufactured by AccuSentry, Inc., for example. Each camera 18 is preferably mounted farther than 1600 mm from the conveyor 13 and the light source is preferably mounted approximately 400 mm from the conveyor. Although a number of cameras are described, a single camera having a high resolution could be employed according to the present invention.

The image capture CCD cameras 18 apply output signals to a computer 20 having a high-speed processor that executes algorithms to process the data. This processor can be, for example, an Intel Pentium 4, 1000 MHz or faster microprocessor. A high-speed connection from the cameras 18 to the processor requires no frame grabber or software to slow the signal.

The image captured by the cameras 18 includes high-contrast white circles on a black background, as shown for example in FIG. 10. The algorithm executed by the processor captures these high contrast ellipsoids across the entire width X of the conveyor 13, allowing the processor to differentiate between individual sheets of glass. As the glass moves under the apparatus, images are captured, ellipses are fit to the ellipsoids, and major and minor axis are measured. Major and minor elliptical axis are measured and correlated to actual distortion in the glass sheets. This algorithm is implemented in real time by software employed by the computer without the need to compare the data to a known flat surface. Results are provided to the unload personnel as the glass arrives to be unloaded. In the preferred embodiment, the light source consists of a pattern of circles 25 mm in diameter spaced across the full width of the light box 15.

The image shown in FIG. 10 comprises high contrast geometrical images or "Features". The image can be either a full size image, either front or rear illuminated, or a projected image. The features can be of any geometrical shape. Specific geometric shapes are most sensitive to specific types of surface distortion. A circle feature is uniquely suited for measuring random distortion. Due to its infinite axes of symmetry, a circle has equal sensitivity to optical distortion along any dimension.

Images from the camera are converted to computer data. That data is processed to computer measurements of the size and shape of the reflected geometric features. For dynamic (moving) objects, measurements are made at either fixed time intervals or time intervals synchronized optically, electronically and/or mechanically with the movement of the object to be measured. A conventional encoding device, such as a rotary signal detector, detects the movement of the glass on the conveyor based upon the rotation of one of the rollers of the conveyor.

A circular geometric feature facilitates computation of surface distortion. The distorted circle appears in reflection as an ellipsoid. A true ellipse fits the feature very closely. The representation of an ellipse is defined by the major radius, minor radius, and angle. These three values provide the information necessary to compute the degree and axis of magnification or demagnification.

Figure 11:
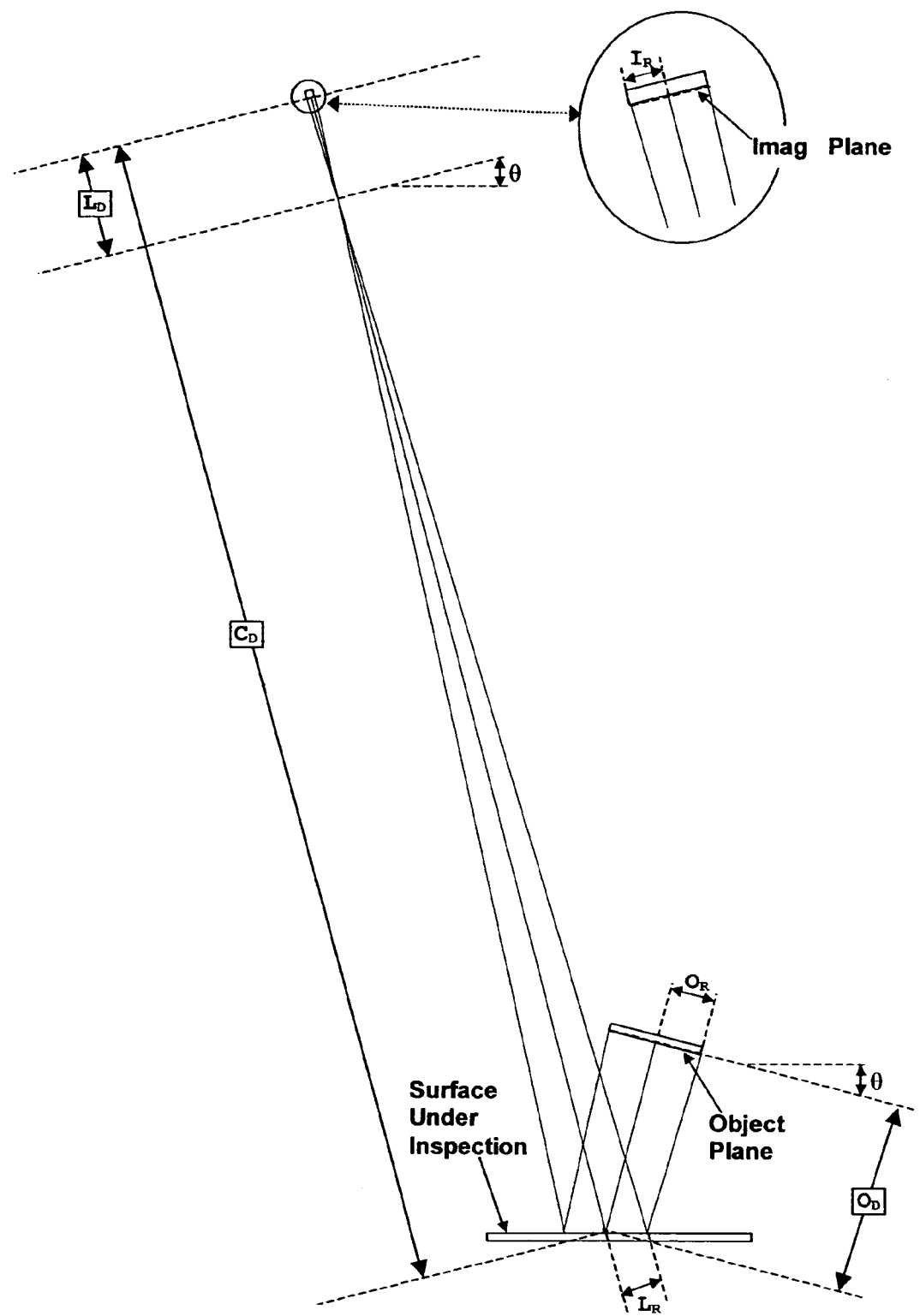
FIG. 11 shows a schematic illustrating a triangle relationship of object and image as measured using the apparatus of the present invention.
Figure 12:
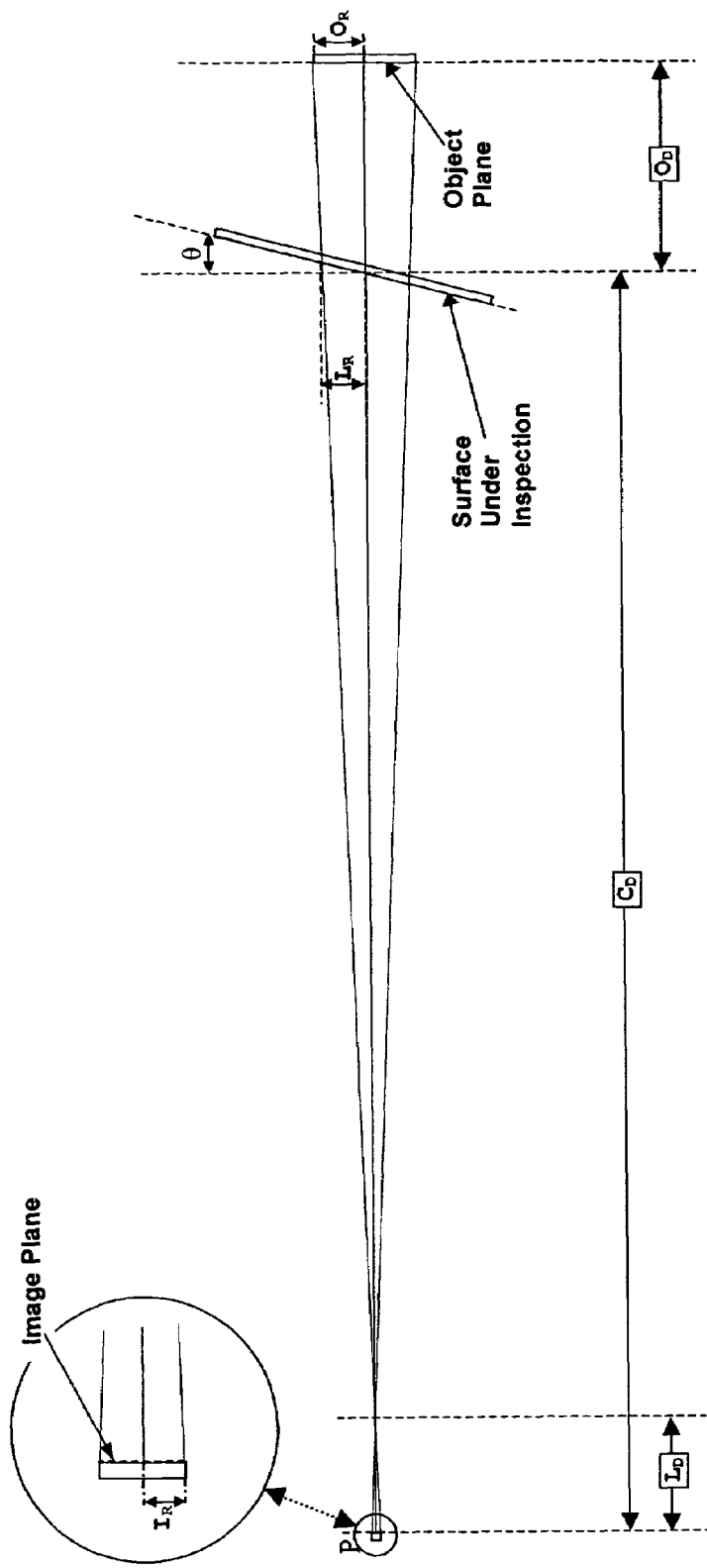
FIG. 12 shows the triangular relationship of FIG. 5 with the optical path unfolded for clarity.

The relationship between the measured feature and the actual feature on the incident image is shown in FIG. 11. FIG. 12 shows an equivalent apparatus with the optical path unfolded for clarity, where $I_R$ is the radius of observed feature;
$L_R$ is the radius of feature on the surface under inspection;
$O_R$ is the radius of the feature on the reference image;
$L_D$ is the focal length of the lens on the video camera;
$C_D$ is the distance from the focal plane of the camera to the surface under inspection;
$O_D$ is the distance from the surface under inspection to the reference image; and
$\Theta$ is the angle between the camera and the surface under inspection as well as the angle between the surface under inspection and the reference image.

Detection of the reflected images from glass sheets passing on the conveyor is accomplished with an area array photo detector such as a digital CCD camera. As glass passes under the light source and camera, the reflected circles are altered by the distortion in the glass. As the circular images traverse the contours of the distorted glass, reflections become elliptical in shape according to the convexity or concavity of the local contours. The camera records images and sends this data to the computer apparatus. The computer apparatus uses this data and calculates the changes in magnification in each ellipsoid and calculates localized lens power in every portion of the sheet. The computer system would compensate for a number of offset parameters in analyzing the reflected images, including the distance of the light source to the glass, the angle of the light source to the glass, the thickness of the glass, etc. the computer system could employ tables which could be accessed depending upon the parameters listed above.

In order to achieve a high contrast image, the projected circles may not be placed so close to each other as to overlap when viewed in reflection and distorted into elliptical shape. To ensure full coverage of measurement over the entire sheet, a series of measurements are made in spatial time. The diffuser image pattern is designed such that as the conveyor moves a distance, 'd', '2d' and '3d', a set of images are captured. When said set of images is overlaid, full coverage is achieved. The apparatus filters the sets of data such that one complete set of magnification data is collected covering the entire area of the sheets. A precision encoding device is preferably attached to the drive train on the conveyor such that the camera(s) may be triggered at precise intervals 'd', '2d' and so on.

The apparatus preferably includes a computer monitor that displays a simplified depiction of the conveyor section. After each load of glass passes under the light source and camera, a depiction of each sheet of glass is shown with color-coding representing the level of distortion in millidiopters or lens power over the each entire sheet. The data for each sheet and load is also stored for generating historical databases, reports, and trend graphs.

This optical apparatus and measurement technique described above have many advantages. The apparatus measures lens power of distortion over the entire surface of any size glass sheet, over the full length (Y) and width (X) of the glass sheets. Distortion in any random pattern at any angle is detected and measured. This significantly improves on prior art devices, which are limited to measuring wave distortion in discrete narrow bands in the direction of glass travel (Y). Such prior art devices assume the distortion in the glass is limited to corrugation in the glass perpendicular to the direction of travel.

The apparatus can be installed over an existing conveyor. The apparatus makes optical distortion measurements on-line with results displayed instantly to the operators. Operators do not have to visually judge distortion level and do not have to remove sheets for off-line testing.

A single light source and camera apparatus is used to measure distortion over the entire area of each sheet at any angle. This significantly improves on prior art devices, which measure distortion in one axis only, that axis being parallel to the direction of travel (Y). Such prior art devices require a plurality of complete optical apparatus including light sources measuring 5¾ inches across and matching sensors. A plurality of such apparatus would be required to measure glass distortions in the sheet widths that are typically tempered, such as 48 to 96 inches in width or greater. The present apparatus uses a single light source to inspect the entire width of the conveyor. The simplicity of this arrangement improves reliability, minimizes maintenance, and decreases cost.

Optical distortion is measured simultaneously for multiple glass sheets as they pass under the light source and camera. In typical heat-treatment apparatus, conveyors are filled with multiple sheets of varying sizes placed randomly. While one load may be a single large sheet covering the entire conveyor, the next may contain sixteen smaller sheets of many sizes. The apparatus of the present invention is capable of measuring each individual sheet of glass and reporting distortion for each sheet of glass. A topographical map of each sheet of glass plus summary data for the load may be viewed by the operator.

All sheets on the conveyor are measured. The full width of the conveyor is scanned continuously. This greatly improves on earlier apparatus that use a single monitoring point. Sheets may be placed in any configuration on the conveyor. There are no lanes to monitor, or to miss, by single point measurement sensors. The continuous array of images provides the data that enables the computer system to locate the lateral edges of individual glass sheets.

Mounting and alignment of the light source and camera apparatus are not critical. The use of a common, diffuse, white light source provides easy installation, operation and maintenance. The light bulbs are commercially available florescent lights. While care should be taken to mount and focus the cameras on the reflection in the glass, alignment by hand and eye is satisfactory. This improves on prior art apparatus using complex, costly lasers and optics requiring many components and exacting alignment.

The apparatus tolerates substantial vibration and movement of the glass sheet inherent in such an industrial environment. Because the method is comparative, no standard value and therefore no periodic calibration are required. Typical bouncing motion of the glass on the conveyor due to vibration does not adversely affect apparatus accuracy. The apparatus measures absolute major and minor diameters, and axes of the ellipses. The relative position of the ellipse to some virtual passline or reference point is unnecessary.

This optical apparatus and measurement technique described above have many advantages. The apparatus measures lens power of distortion over the entire surface of any size glass sheet, over the full length (Y) and width (X) of the glass sheets. Distortion in any random pattern at any angle is detected and measured. This significantly improves on prior art devices, which are limited to measuring wave distortion in discrete narrow bands in the direction of glass travel (Y). Such prior art devices assume the distortion in the glass is limited to corrugation in the glass perpendicular to the direction of travel.

The apparatus can be installed over an existing conveyor. The apparatus makes optical distortion measurements on-line with results displayed instantly to the operators. Operators do not have to visually judge distortion level and do not have to remove sheets for off-line testing.

A single light source and camera apparatus is used to measure distortion over the entire area of each sheet at any angle. This significantly improves on prior art devices, which measure distortion in one axis only, that axis being parallel to the direction of travel (Y). Such prior art devices require a plurality of complete optical apparatus including light sources measuring 5-3/4 inches across and matching sensors. A plurality of such apparatus would be required to measure glass distortions in the sheet widths that are typically tempered, such as 48 to 96 inches in width or greater. The present apparatus uses a single light source to inspect the entire width of the conveyor. The simplicity of this arrangement improves reliability, minimizes maintenance, and decreases cost.

Optical distortion is measured simultaneously for multiple glass sheets as they pass under the light source and camera. In typical heat-treatment apparatus, conveyors are filled with multiple sheets of varying sizes placed randomly. While one load may be a single large sheet covering the entire conveyor, the next may contain sixteen smaller sheets of many sizes. The apparatus of the present invention is capable of measuring each individual sheet of glass and reporting distortion for each sheet of glass. A topographical map of each sheet of glass plus summary data for the load may be viewed by the operator.

All sheets on the conveyor are measured. The full width of the conveyor is scanned continuously. This greatly improves on earlier apparatus that use a single monitoring point. Sheets may be placed in any configuration on the conveyor. There are no lanes to monitor, or to miss, by single point measurement sensors. The continuous array of images provides the data that enables the computer system to locate the lateral edges of individual glass sheets.

Mounting and alignment of the light source and camera apparatus are not critical. The use of a common, diffuse, white light source provides easy installation, operation and maintenance. The light bulbs are commercially available florescent lights. While care should be taken to mount and focus the cameras on the reflection in the glass, alignment by hand and eye is satisfactory. This improves on prior art apparatus using complex, costly lasers and optics requiring many components and exacting alignment.

The apparatus tolerates substantial vibration and movement of the glass sheet inherent in such an industrial environment. Because the method is comparative, no standard value and therefore no periodic calibration are required. Typical bouncing motion of the glass on the conveyor due to vibration does not adversely affect apparatus accuracy. The apparatus measures absolute major and minor diameters, and axes of the ellipses. The relative position of the ellipse to some virtual passline or reference point is unnecessary.

The foregoing detailed description has discussed only a few of the many forms that this invention can take. For this reason, this detailed description is intended by way of illustration, and not by way of limitation. It is only the following claims, including all equivalents, that are intended to define the scope of this invention.

The invention claimed is:

1. An apparatus for measuring optical distortion in a transmissive reflective sheet, the apparatus comprising:
   a conveyor receiving and positioning the transmissive reflective sheet, with the conveyor having a length in a transport direction and a width transverse to the length and coextensive with the conveyor;
   a light source mounted on a first side of the conveyor, the light source projecting a plurality of ellipsoidal two-dimensional images across the length and the width of the conveyor wherein the plurality of two-dimensional images appear continuously and simultaneously on the transmissive reflective sheet, with the plurality of two-dimensional images separated and regularly spaced about the length of the conveyor, with the plurality of two-dimensional images separated and regularly spaced about the width of the conveyor, with each of the plurality of two-dimensional images separated from all others of the plurality of two-dimensional images by a background, with each of the plurality of two-dimensional images regularly spaced from each adjacent one of the plurality of two-dimensional images, with the plurality of two-dimensional images being high-contrast white in color and the background being black in color, wherein the high-contrast white in color of the plurality of two-dimensional images is different from the black of the background and detectable by the camera, and with the plurality of two-dimensional images reflected off the transmissive reflective sheet and producing a plurality of reflected two-dimensional images;

a camera oriented to continuously and simultaneously detect the plurality of reflected two-dimensional images corresponding to the plurality of two-dimensional images; and a processing circuit coupled to receive output data from the camera to:

measure magnification and orientation of each of the plurality of reflected two-dimensional images; and compute lens power based on a measurement of magnification of the reflected two-dimensional images, wherein the lens power is indicative of a local curvature of the transmissive reflective sheet over the the length and the width of the conveyor.

2. The apparatus of claim 1 wherein the camera is positioned on the first side of the conveyor.

3. The apparatus of claim 1 wherein the camera is positioned on an opposite side of the transmissive reflective sheet from the light source to detect a plurality of transmitted two-dimensional images of the plurality of two-dimensional images.

4. An apparatus for measuring optical distortion in a transmissive reflective glass sheet, the apparatus comprising:

a conveyor receiving and positioning the transmissive reflective glass sheet, with the conveyor having a length in a transport direction and a width transverse to the length and coextensive with the conveyor;

a light source mounted on a first side of the conveyor, the light source projecting a plurality of images across the length and the width of the conveyor wherein the plurality of images appear continuously and simultaneously on the transmissive reflective glass sheet, with each of the plurality of images having a circumference, a center, a major axis extending through the center from two major points opposite and greatest spaced from each other on the circumference, a minor axis extending through the center from two minor points opposite and least spaced from each other on the circumference, and an angle between the major axis and the minor axis, with the plurality of images reflected off the transmissive reflective glass sheet producing a plurality of reflected images;

a camera mounted on the first side of the conveyor and oriented to detect the plurality of reflected images each corresponding to one of the plurality of images, with each of the plurality of reflected images having a reflected circumference, a reflected center, a reflected major axis extending through the reflected center from two reflected major points opposite and greatest spaced from each other on the reflected circumference, a reflected minor axis extending through the reflected center from two reflected minor points opposite and least spaced from each other on the reflected circumference, and a reflected angle between the reflected major axis and the reflected minor axis;

a motion detector coupled to the conveyor to measure motion of the transmissive reflective glass sheet and trigger the camera at predetermined intervals; and a processing circuit coupled to receive output data from the camera to:

measure magnification and orientation of each of the plurality of reflected images, wherein the magnification is a ratio of the reflected major axis to the major axis and a ratio of the reflected minor axis to the minor axis of each of the plurality of reflected images, and the orientation is a difference between the reflected angle and the angle; and compute lens power of each of the plurality of reflected images based on the magnification of each of the plurality of reflected images, wherein the lens power is indicative of local curvature of the transmissive reflective glass sheet over the length and the width of the conveyor.

5. The apparatus of claim 4 wherein each of the plurality of images are ellipsoids, with each of the plurality of images separated from all others of the plurality of images by a background, with each of the plurality of images regularly spaced from each adjacent one of the plurality of images, with the plurality of images being high-contrast white in color and the background being black in color, wherein the high-contrast white in color of the plurality of two-dimensional images is different from the black of the background and detectable by the camera.

6. The apparatus of claim 4 further comprising a thickness sensor coupled to the conveyor.

7. The apparatus of claim 4 wherein the light source comprises a point light source and a reticle.

8. The apparatus of claim 4 wherein the processing circuit is further coupled to receive a plurality of offset parameters selected from a distance of the light source to the transmissive reflective glass sheet, an angle of the light source to the transmissive reflective glass sheet and a thickness of the transmissive reflective glass sheet.

9. An apparatus for measuring optical distortion in a transmissive reflective sheet of glass, the apparatus comprising:

a conveyor for receiving and positioning a plurality of transmissive reflective sheets of glass, the conveyor having a length in a transport direction and a width transverse to the length and coextensive with the conveyor;

a light source mounted on a first side of the conveyor, the light source projecting a plurality of images in a prescribed pattern across the width and the length of the conveyor wherein the plurality of images appear continuously and simultaneously as a plurality of circles on one of the plurality of transmissive reflective sheets of glass, with the plurality of images each having a circumference, a center and a plurality of axes extending through the center between opposite points on the circumference and defining a diameter, with each of the plurality of axes distinct from one another, with the plurality of images reflected off the one of the plurality of transmissive reflective sheets of glass producing a plurality of reflected images;

a camera mounted on the first side of the conveyor and oriented to detect the plurality of reflected images corresponding to the plurality of images, with the plurality of reflected images each having a reflected circumference, a central point and a plurality of reflected axes extending through the central point between opposite reflected points of the reflected circumference and defining a reflected diameter, with each of the plurality of reflected axes distinct from one another;

a motion detector coupled to the conveyor to measure motion of the one of the transmissive reflective sheets of glass and trigger the camera at precise intervals;

a thickness detector coupled to the conveyor to measure thickness of the one of the transmissive reflective sheets of glass; and a processor coupled to receive output data from the camera to:

measure magnification and orientation of the plurality of reflected images, wherein the magnification is a ratio of a reflected diameter to a corresponding diameter of each of the plurality of reflected images and the orientation corresponds to one of the plurality of reflected axes with a greatest magnification of each of the plurality of reflected images;

compute lens power based on the magnification of each of the plurality of reflected images, and derive the lens power in any orientation about the plurality of axes of each of the plurality of reflected images over all areas of the one of the transmissive reflective sheets of glass, wherein the lens power is indicative of local curvature of the one of the transmissive reflective sheets of glass over the length and the width of the conveyor.

10. A method of measuring optical distortion in a transmissive reflective sheet, the method comprising:

positioning the transmissive reflective sheet on a conveyor, with the conveyor having a length in a transport direction and a width transverse to the length and coextensive with the conveyor;

projecting a plurality of images continuously and simultaneously across the length and the width of the conveyor with the plurality of images appearing on the transmissive reflective sheet, with projecting the plurality of images comprising: separating and regularly spacing the plurality of images about the length and the width of the conveyor, with each of the plurality of images being ellipsoidal, separating each of the plurality of images from all others of the plurality of images by a background, and spacing each of the plurality of images regularly from each adjacent one of the plurality of images, with the plurality of images being high-contrast white in color and the background being black in color;

detecting a difference in contrast in the plurality of images and the background;

reflecting the plurality of images off the transmissive reflective sheet and producing a plurality of reflected images;

detecting continuously and simultaneously the plurality of reflected images corresponding to the plurality of images;

measuring magnification and orientation of each of the plurality of reflected images; and computing lens power based on the magnification of the plurality of reflected images, wherein the lens power is indicative of local curvature of the transmissive reflective sheet over the length and the width of the conveyor.

11. The method of claim 10 further comprising detecting motion of the transmissive reflective sheet.

12. The method of claim 10 wherein detecting comprises triggering a camera at predetermined intervals.

13. The method of claim 10 further comprising measuring thickness of the transmissive reflective sheet.

14. The method of claim 10 further comprising storing offset parameters including a thickness of the transmissive reflective sheet.

15. A method of measuring optical distortion in a transmissive reflective glass sheet, the method comprising:

positioning the transmissive reflective glass sheet on a conveyor, with the conveyor having a length in a transport direction and a width transverse to the length and coextensive with the conveyor;

projecting a plurality of images continuously and simultaneously on the transmissive reflective glass sheet, with each of the plurality of images having a circumference, a center, a major axis extending through the center from two major points opposite and greatest spaced from each other on the circumference, a minor axis extending through the center from two minor points opposite and least spaced from each other on the circumference, and an angle between the major axis and the minor axis;

reflecting each of the plurality of images off the transmissive reflective glass sheet and producing a plurality of reflected images;

detecting motion of the transmissive reflective glass sheet;

triggering a camera at a predetermined interval;

detecting the plurality of reflected images from the transmissive reflective glass sheet, with each of the plurality of reflected images having a reflected circumference, a reflected center, a reflected major axis extending through the reflected center from two reflected major points opposite and greatest spaced from each other on the reflected circumference, a reflected minor axis extending through the reflected center from two reflected minor points opposite and least spaced from each other on the reflected circumference, and a reflected angle between the reflected major axis and the reflected minor axis;

measuring thickness of the transmissive reflective glass sheet on-line;

receiving output data from the camera to measure magnification and orientation of the plurality of reflected images, wherein measuring the magnification is taking a ratio of the reflected major axis to the major axis and a ratio of the reflected minor axis to the minor axis of each of the plurality of reflected images, and measuring the orientation is determining a difference between the reflected angle and the angle; and computing lens power based on measuring the magnification of the plurality of reflected images, with the lens power indicating local curvature of the transmissive reflective glass sheet over the length and the width of the conveyor, with each of the plurality of images having a position along the length and the width of the conveyor, with each of the plurality of reflected images having a reflected position along the length and the width of the conveyor, with positioning the transmissive reflective glass sheet changing the position of each of the plurality of images and the reflected position of each of the plurality of reflected images, with computing the lens power not using the position of each of the plurality of images along the length and the width of the conveyor, and with computing the lens power not using the reflected position of each of the plurality of reflected images along the length and the width of the conveyor.

16. The method of claim 15 wherein detecting motion of the transmissive reflective glass sheet comprises using a sensor to detect movement of the transmissive reflective glass sheet across the conveyor.

17. The method of claim 15 wherein projecting a plurality of images on the transmissive reflective glass sheet comprises projecting images from a diffuse light source producing polychromatic light in the visible spectral range.

18. The method of claim 15 wherein projecting a plurality of images on the transmissive reflective glass sheet comprises projecting an image using a point light source and a reticle.

19. A method of measuring lens optical distortion in sheets of glass, the method comprising:

positioning a plurality of sheets of glass on a conveyor, with the conveyor having a length in a transport direction and a width transverse to the length and coextensive with the conveyor;

projecting a plurality of images of light in a prescribed pattern across the width and the length of the conveyor such that the plurality of images appear continuously and simultaneously as circles on one of the plurality of sheets of glass, with the plurality of images each having a circumference, a center and a plurality of axes extending through the center and between opposite points on the circumference and defining a diameter, with each of the plurality of axes distinct from one another;

reflecting each of the plurality of images off the one of the plurality of sheets of glass and producing a plurality of reflected images;

measuring motion of the one of the plurality of sheets of glass;

triggering a camera at precise intervals;

measuring thickness of each of the plurality of sheets of glass on-line;

detecting the plurality of reflected images corresponding to the plurality of images with a camera, with the plurality of reflected images each having a reflected circumference, a central point and a plurality of reflected axes extending through the central point from opposite reflected points on the circumference and defining a reflected diameter, with each of the plurality of reflected axes distinct from one another;

calibrating the plurality of reflected images to account for lens aberration due to varying distance between the plurality of images and the lens and due to various thicknesses of glass;

processing output data from the camera to measure magnification and orientation of the plurality of reflected images, wherein measuring the magnification is taking a ratio of the reflected diameter to a corresponding diameter of each of the plurality of reflected images and measuring the orientation is determining one of the plurality of reflected axes with the greatest magnification of each of the plurality of reflected images, and with processing output data further comprising deriving lens power in any orientation about the plurality of axes of each of the plurality of reflected images over the length and the width of the conveyor; and computing the lens power based on measuring the magnification of each of the plurality of reflected images, with the lens power indicating local curvature of the one of the plurality of sheets of glass over the length and the width of the conveyor.

20. An apparatus for measuring optical distortion in a reflective substrate using lens power, the apparatus comprising:

a conveyor operative to convey a reflective substrate;

a light source operative to project a two-dimensional image on the reflective substrate, with the two-dimensional image having a circumference, a center, a major axis extending through the center from two major points opposite and most spaced from each other on the circumference, a minor axis extending through the center from two minor points opposite and least spaced from each other on the circumference, and an angle between the major axis and the minor axis, wherein the reflective substrate reflects the two-dimensional image as a reflected two dimensional image;

a detector positioned to detect the reflected two-dimensional image; and circuitry operative to:

measure magnification of the two-dimensional image in the reflected two-dimensional image, with the reflected two-dimensional image having a reflected circumference, a reflected center, a reflected major axis extending through the reflected center from two reflected major points opposite and greatest spaced from each other on the reflected circumference, a reflected minor axis extending through the reflected center from two reflected minor points opposite and least spaced from each other on the reflected circumference, and a reflected angle between the reflected major axis and the reflected minor axis; and compute lens power based on a measurement of the magnification wherein magnification is a ratio of the reflected major axis to the major axis and a ratio of the reflected minor axis to the minor axis of each of the plurality of reflected images, wherein the lens power is indicative of local curvature of the reflective substrate over the length and the width of the conveyor, with the two-dimensional image having a position along the length and the width of the conveyor, with the reflected two-dimensional image having a reflected position along the length and the width of the conveyor, with the lens power not based on the position of the two-dimensional image along the length and the width of the conveyor, and with the lens power not based on the reflected position of the two-dimensional images along the length and the width of the conveyor.

21. The apparatus of claim 20, wherein the reflective substrate comprises a flat sheet of glass.

22. The apparatus of claim 20, wherein the conveyor has a length in a transport direction and a width transverse to the length and coextensive with the conveyor and the light source is operative to project a plurality of two-dimensional images across the width and the length of the conveyor.

23. The apparatus of claim 20, wherein the two-dimensional image comprises a circle, and wherein the reflected two-dimensional image comprises an ellipse.

24. The apparatus of claim 20, wherein the detector comprises at least one camera.

25. The apparatus of claim 20 further comprising a thickness detector operative to measure a thickness of the reflective substrate, and wherein the circuitry is further operative to compensate the measurement of the magnification based on measured thickness.

26. The apparatus of claim 20, wherein the circuitry comprises a processor.

* * * * *